United States Patent
Stolpman et al.

(10) Patent No.: US 8,736,486 B2
(45) Date of Patent: May 27, 2014

(54) SYNTHETIC APERTURE RADAR SYSTEM

(75) Inventors: James L. Stolpman, Bloomingdale, IL (US); Hans-Joachim Fabry, Berlin (DE); Todd R. Henry, Arlington Heights, IL (US)

(73) Assignee: Interstitial, LLC, Mt. Prospect, IL (US)

( * ) Notice: Subject to any disclaimer, the term of this patent is extended or adjusted under 35 U.S.C. 154(b) by 0 days.

(21) Appl. No.: 12/317,636

(22) Filed: Dec. 23, 2008

(65) Prior Publication Data

US 2009/0309786 A1  Dec. 17, 2009

Related U.S. Application Data

(60) Provisional application No. 61/009,449, filed on Dec. 28, 2007.

(51) Int. Cl.
*G01S 7/40* (2006.01)
*G01S 13/90* (2006.01)

(52) U.S. Cl.
USPC .................................... 342/165; 342/25 A

(58) Field of Classification Search
USPC ........................................................ 342/165
See application file for complete search history.

(56) References Cited

U.S. PATENT DOCUMENTS

| | | | | |
|---|---|---|---|---|
| 4,774,961 | A * | 10/1988 | Carr | 600/549 |
| 5,682,165 | A * | 10/1997 | Lewis et al. | 342/174 |
| 5,829,437 | A * | 11/1998 | Bridges | 600/430 |
| 6,061,589 | A * | 5/2000 | Bridges et al. | 600/430 |
| 7,340,292 | B2 * | 3/2008 | Li | 600/430 |
| 2004/0097811 | A1 | 5/2004 | Smith et al. | |
| 2005/0107693 | A1 | 5/2005 | Fear et al. | |
| 2005/0251235 | A1 | 11/2005 | Schlorff et al. | |
| 2006/0103392 | A1 | 5/2006 | Martens et al. | |
| 2007/0060816 | A1 | 3/2007 | Simpkin | |
| 2007/0073144 | A1 * | 3/2007 | Simpkin | 600/430 |
| 2007/0293752 | A1 * | 12/2007 | Simpkin | 600/407 |
| 2008/0071169 | A1 * | 3/2008 | Craddock et al. | 600/430 |
| 2010/0069744 | A1 * | 3/2010 | Simpkin | 600/425 |

FOREIGN PATENT DOCUMENTS

WO  2007/054685 A2  5/2007

OTHER PUBLICATIONS

International Search Report and Written Opinion, etc., dated Mar. 3, 2009 re PCT/US2008/14061.
International Preliminary Report on Patentability dated Jul. 8, 2010 re PCT/US2008/14061.
European Patent Office Supplementary European Search Report dated Oct. 18, 2013 for European Patent Application 08867637.4, 3 pages.
European Patent Office Examination Report dated Nov. 12, 2013 for European Patent Application 08867637.4, 4 pages.

* cited by examiner

*Primary Examiner* — Matthew M Barker
(74) *Attorney, Agent, or Firm* — Fitch, Even, Tabin & Flannery, LLP

(57) ABSTRACT

An imaging system for generating a three dimensional image of tissue of a patient is provided. The imaging system comprises of a transmitter, receiver, antenna system and a display element to form a synthetic aperture radar system that displays a three dimensional view of the tissue. The SAR system has been configured to operate in the near field as opposed to current equipment which can only perform satisfactorily in the far field. A calibration technique has been utilized that allows the system to perform as well as other systems that operate using far field techniques but allows for a much simpler, cost effective system.

22 Claims, 6 Drawing Sheets

SYNTHETIC APERTURE RADAR SYSTEM

RELATED APPLICATIONS

The present application claims priority to provisional application U.S. Ser. No. 61/009,449, filed on Dec. 28, 2007 the entire disclosure of which is hereby incorporated by reference.

TECHNICAL FIELD OF THE INVENTION

The present device relates to radar systems. Particularly, the present device relates to synthetic aperture radar systems, such as used in the near field to detect cancer.

BACKGROUND OF THE INVENTION

Breast cancer is one of the leading causes of death for women. About one out of eight or nine women are expected to develop tumors of the breast, and about one out of sixteen to twenty are expected to die prematurely from breast cancer.

Mammography or other X-ray methods are currently most used for detection of breast cancers. However, every time a mammogram is taken, the patient incurs a small risk of having a breast tumor induced by the ionizing radiation properties of the X-rays used during the mammogram. Also, the process is costly and sometimes imprecise. Accordingly, the National Cancer Institute has not recommended mammograms for women under fifty years of age, who are not as likely to develop breast cancers as are older women. However, while only about twenty percent of breast cancers occur in women under fifty, data suggests that breast cancer is more aggressive in pre-menopausal women. Furthermore, women under forty are getting the disease in increasing numbers—about eleven thousand annually now—and no one knows why.

Mammograms require interpretation by radiologists. Radiologist can identify cancers between five and ten millimeters in diameter. Generally, when detected at this stage, the prognosis is favorable. However, about ten to fifteen percent of tumors this size are not detected. One study showed major clinical disagreements for about one-third of the same mammograms that were interpreted by a group of radiologists. Further, many women find that undergoing a mammogram is a decidedly painful experience.

Thus, alternative methods to detect breast cancer are needed, especially those that do not entail added risks; that can detect tumors as small as two millimeters in diameter; that are not unduly unpleasant to the patient; and that can be used for mass screening. A screening system is needed because extensive studies have demonstrated that early detection of small breast tumors leads to the most effective treatment. While X-ray mammography can detect lesions of approximately five mm or larger, the accuracy may range between 30% and 75%, depending on the skill of the diagnostic radiologist. Repeated X-ray examinations, however, are not encouraged because, as discussed above, may actually induce cancer formation. These considerations, in addition to costs, have led physicians to recommend that women wait until the age of fifty before having routine mammograms.

One solution would be a non-ionizing, noninvasive, and low cost detection or screening method. It could greatly increase the number of patients examined and would identify those patients who need diagnostic X-ray examinations, where the added hazards and costs could be justified. Thus, there is a need for a low-cost, noninvasive, screening method.

There are several generic detection methods: sonic, chemical, nuclear and non-ionizing electromagnetic. The sonic, chemical and nuclear (such as MRI) techniques have been under study for some time and, while some interesting approaches are being followed, none have been publicized as being available in the near future for low cost screening.

Non-ionizing electromagnetic methods have also been under investigation. Studies have considered the use of electromagnetic, non-ionizing methods to detect or image portions of the human body. One summary of such activity is presented in a publication entitled "Medical Applications of Microwave Imaging." edited by L. E. Larsen and J. H. Jacobi, IEEE Press 1986. These activities include microwave thermography, radar techniques to image biological tissues, microwave holography and tomography, video pulse radar, frequency modulation pulse compression techniques for biological imaging, microwave imaging with diffraction tomography, inverse scattering approaches, and medical imaging using an electrical impedance. The technology cited not only includes electromagnetic disciplines, but also notes related studies in sonic imaging and seismic imaging.

Many important reasons exist for the lack of progress in these areas. In the case of microwave thermography, adequate depth of penetration, along with the required resolution, may not be realized, except for large cancers. In the case of other techniques using electromagnetic activities, reflections at the skin-air surface tend to mask the desired returns from breast tumors beneath the skin. Further, illuminating the entire volume of a breast either requires excessive power (with possible biological hazards) or acceptance of poor signal-to-noise rations. In the case of through-the-body electromagnetic techniques, such as tomography, the attenuation characteristics of the body are such that long wavelengths are usually used, with an attendant loss of resolution. Another important reason for the lack of progress is the degradation of sensitivity due to insufficient characterization techniques available for the antenna setups in near field. As the usable wavelengths are restricted by the attenuation characteristics of the body, all known techniques have to place the sensors, like antennas or antenna arrays, in close vicinity of the body parts to be examined.

Far field systems have been developed to overcome these limitations by placing the antennas at a distance of at least five to ten wavelengths away from the surface of the body part under examination so the signal being radiated has local plane-wave characteristics in order to correctly interpret the reflected measured response. Further, increasing the distance helps to minimize changes of the antenna characteristics through distortions of the electromagnetic field caused by direct interactions between the antenna structures and the body parts under examination. Additionally, multiple reflections between the antennas of the system and the skin-air interface of the body parts under examination may mask the desired returns from tumors and degrade the capability to detect cancers. Far field systems also require the use of much higher frequencies than near field system to reduce the absolute distance between antenna and the surface of the body parts to be scanned, as the far field regions is defined as a distance of at least ten wavelengths.

Certain near field systems have been described in the literature immersing the antenna/antennae and body parts under examination into a homogenous liquid solution with dielectric properties similar to the body parts in an attempt to make accurate measurements. While this approach helps to reduce some of the effects to a certain amount, it adds inconveniencies to the examination. The additional measures to be taken to make components watertight adds significant costs to the system it-self. Even when using liquid solutions to reduce the reflections on the skin-air interface, the large variation in electrical properties between the breast tissues of different women at different ages account for mismatch errors during measurements, if the dielectric properties of the liquids don't exactly match those of the tissue.

SUMMARY OF THE INVENTION

There is disclosed herein an improved radar system which avoids the disadvantages of prior devices while affording additional structural and operating advantages.

According to one form, a method for calibrating a near field synthetic aperture radar system is provided. The method includes the steps of positioning at least one antenna adjacent an object to be scanned; scanning a reflecting material using the at least one antenna to create a scanning profile; scanning an absorbing material using the at least one antenna to create an absorbing profile; and creating a calibrated profile using the scanning profile and the absorbing profile.

In one form, a system is provided for determining localized differences in human tissue. The system includes at least one antenna, a reflecting material, an absorbing material and a calibrator. The at least one antenna is included for transmitting and receiving a signal in near field uses. The reflecting material is positioned adjacent the at least one antenna in a first calibration configuration. The absorbing material is positioned adjacent the at least one antenna in a second calibration configuration. In the first calibration configuration, the antenna creates a first calibration profile. In the second calibration configuration, the antenna creates a second calibration profile using a single port calibration method. A single port calibration method is one in which a single port is used as both as the signal source and as the port point at which the reflected signal is measured by the signal generating and measuring equipment. A multiple port method may be used in which the received signal is separated from the transmitted signal after being received by the antenna and connected to a second or additional port of the signal generating and measuring equipment. Another multiple port method may be utilized in which separate antennae are used, so that each port of the signal generating and measuring equipment is connected to a different antenna. Additionally, the calibrator determines an error profile.

According to one form, the at least one antenna is positioned a distance from the object to be scanned, the distance defining an air gap.

In accordance with one form, human tissue is scanned to create an uncalibrated profile and the calibrator creates a corrected profile using the calibrated profile and the error profile.

In one form, the corrected profile is a three-dimensional profile.

According to one form, the calibrator uses a single port calibration method.

In accordance with one form, the calibrator uses a multiple port calibration method.

According to one form, the at least one antenna is movable for scanning at multiple positions.

In one form, a single antenna may be use and moved to multiple positions to make measurements but all the positions of the antenna lie in single geometric plane for all measurements.

In one form, a single antenna may used and may be moved in three dimensions to form a non-coplanar surface where in the positions of the antenna define a geometric shape that is not a geometric plane.

In one form, more than antenna may be used and may or may not be moved but all the antennae and antennae positions lie in a single geometric plane for all measurements.

In one form, more than one antenna may be use in which the surface described by the positions of the antennae do not lie on a geometric plane. The antennae may be fixed or may be moved to make measurements.

According to one form, human tissue is the absorbing material.

In one form, the antenna is printed on a flexible material.

These and other aspects of the invention may be understood more readily from the following description and the appended drawings.

BRIEF DESCRIPTION OF THE DRAWINGS

For the purpose of facilitating an understanding of the subject matter sought to be protected, there are illustrated in the accompanying drawings embodiments thereof, from an inspection of which, when considered in connection with the following description, the subject matter sought to be protected, its construction and operation, and many of its advantages should be readily understood and appreciated.

DETAILED DESCRIPTION OF PREFERRED EMBODIMENTS

Figure 1:
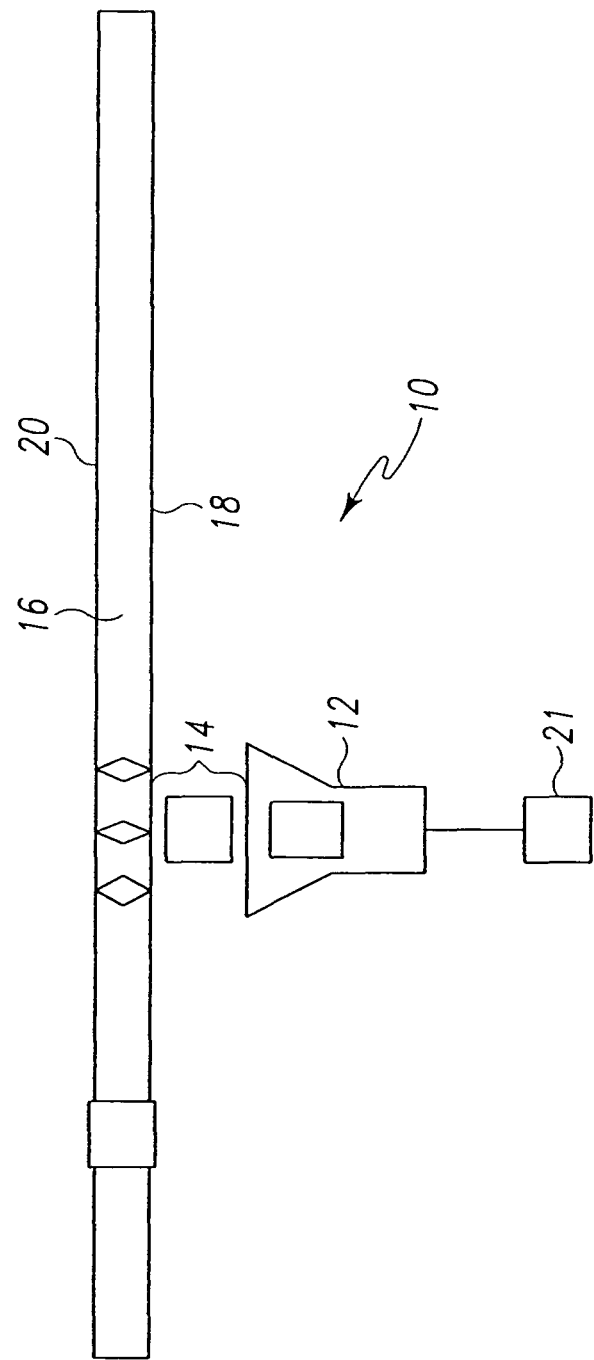
FIG. 1 is a somewhat schematic representation showing a radar system.

While this invention is susceptible of embodiments in many different forms, there is shown in the drawings and will herein be described in detail a preferred embodiment of the invention with the understanding that the present disclosure is to be considered as an exemplification of the principles of the invention and is not intended to limit the broad aspect of the invention to embodiments illustrated.

A radar system either emits a broadband pulse or a series of stepped frequencies to illuminate the target. The energy reflected from the target's radar cross section (RCS) is received and correlated to the emitted pulse or spectra. Because the exact shape of the emitted pulse/spectra is unknown, the a priori knowledge of the system response is important for proper signal detection.

Conventional radar systems generate a short pulse, whose traveling time from the radar antenna to the target and it's reflection from the target back to the antenna is taken as a reference for the distance of the target to the radar antenna. By knowing the electrical properties of the media the radar pulse is traveling through, one can calculate the distance between radar antenna and target. The spatial resolution of the radar, or the ability to locate a target in free space, is accomplished by rotating the antenna and transmitting a series of pulses while the antenna is moving For a good resolution of the distance, the so called range resolution, the radar pulse has be as short as possible. Unfortunately, with a shorter pulse, the transmitted power is lowered, decreasing the maximum range of the radar.

If the pulse is transmitted by the transmitter of a pulsed radar system, this pulse is also detected by the radar system's receiver. As the power of the pulse is quite high, no other signal can be received for the duration of the pulse, as it masks all the other (weaker) signals reflected by the targets. During the duration of the pulse the electro magnetic wave is traveling in free space with the speed of light, so all targets in a round-trip distance (the distance from antenna to the target and back) shorter than the distance defined by the pulse width can not be detected. A pulse width of 1 µs creates a 'deaf' area of about 300.000 km/s*0.000001 s=150 m around the antenna where the radar can't detect a target.

Several techniques to overcome these limitations, such as chirp compression or pulse compression, have been developed during the last fifty years, but still the minimum detection distance of conventional pulsed radar systems lies in the range of some ten to hundred yards, depending on the frequencies used.

Another technique uses stepped continuous wave (cw) frequencies over a frequency band to illuminate the target. As this collection of equally spaced frequencies can be treated as the spectrum of a synthetic pulse, the pulse itself and the target response can be calculated from the responses at the single frequencies using an inverse fourier transformation. While this method offers enhanced resolution, the sensitivity is limited by the fact that the radar system is continuously transmitting and receiving at the same frequencies and signals which are directly coupled from the transmitter to the receiver are reducing the dynamic range of the receiver.

Different methods have been developed over the years to increase the sensitivity and resolution of radar systems. As the sensitivity of a radar increases with increasing antenna size, a technique is used where a virtual antenna is formed by placing or moving much smaller antennae along a path while making measurements. By combining the results of several single measurements taken at exactly known antenna positions, the target response can be calculated, which is magnified as if a single large antenna of a size covering all the positions of the small antenna would have been used. By delaying the response of single antenna positions either electronically or by algorithm, the focal point of the synthetic aperture formed by the single antenna position can be moved without actually moving the position of the smaller antennae. This kind of radar application is usually called synthetic aperture radar or SAR.

As a SAR combines the data from several different antenna positions or antennas into an image, the exact spatial location of each antenna position and the exact properties for each antenna have to be taken into account. Not knowing the exact location of the single antenna positions may make it difficult or even impossible to calculate the location of the target as a correct triangulation may not be possible. The calculation also may not be done correctly if the antenna radiation pattern of the antennae at the operating frequencies is unknown as the algorithms used for triangulation depend on the known phase relationship between the different antenna positions. The electromagnetic properties of the antennae used in SAR systems are usually determined by mounting the antenna into a test range where the antenna's radiation pattern is characterized. By knowing the antenna radiation pattern, a correction function for the antenna can be calculated, which, when applied to the received signals, improves the sensitivity and spatial resolution of the radar system by equalizing the magnitude and phase response of the antenna system.

The detection of changes in body tissues by imaging the body parts using electromagnetic waves generally follows the same principles like other radar systems. Whereas the frequencies for radar systems operating in free space applications can be selected in a wide frequency range for better resolution, the frequencies for the detection of anomalies in body tissues are restricted to a relatively low frequency range due to the electrical properties of the human tissues.

Based on the work conducted by C. Gabriel, a model was developed at the Italian Istituto di Fisica Applicata "Nello Carrara" IFAC which allows the calculation for dielectrical dielectric properties of different human body tissues at selectable frequencies. (C. Gabriel and S. Gabriel, "Compilation of the Dielectric Properties of Body Tissues at RF and Microwave Frequencies", Armstrong Laboratory (AFMC), Report Number AL/OE-TR-1996-0037). The model calculates a penetration depth into breast tissue of 1.4 cm at a frequency of 10 GHz. It is clearly visible that a system using electromagnetic waves for the detection of breast cancer needs to utilize frequencies which are lower than 10 GHz to achieve enough penetration depth into the body tissue.

One additional problem arises when using wavelengths in the range of 3 cm and longer. If the antenna of the radar system has to be placed in far field to achieve the required uniformity of the antenna radiation pattern, the distance between the antenna and the body part under examination has to be a minimum of 10 wavelengths, resulting into 3 m if the system is utilizing frequencies in the range of 1 GHz and higher. According to the formula for path losses in free space $$\text{Path\_Loss(dB)} = 32.44 + 20*\log(f(\text{MHz})) + 20*\log(d(\text{km})) - GainTX(\text{dB}) - GainRX(\text{dB})$$

the path loss for a system using a dipole antenna with a gain of 2.14dB at a distance of 3m from the body part equals 63.7dB. The distance counts twice as the incident electromagnetic wave is traveling the distance from the antenna to the body part and the reflected portion is traveling the same distance back to the antenna.

The combination of the path loss with the relatively high attenuation of the electromagnetic waves in human body tissue results in high requirements in the circuitry of the radar system as the dynamic range needed to cope with the losses easily exceeding 100 dB or more. Generally the achievable dynamic range for systems working with continuous waves and utilizing one or more transmit and receive antennas lies in the range of 60 dB to 80 dB. The dynamic range is limited by the directional components of the radar system which are needed to separate the incident signal generated by the transmitter and the reflected signal portion scattered back from the target. As transmitting and receiving frequencies are the same, the much stronger transmitted signal tends to mask out the much weaker back scattered portion. The problem remains if different transmit and receive antennae are used because of the direct coupling between the antennas, which is equal to the free space loss between the antennae, multiplied with the antennae radiation pattern for the corresponding angle.

Therefore, a radar system using electromagnetic waves for the detection of changes in body tissues preferably needs to locate the antennae as near as possible to the vicinity of the body part under examination. This means that at the usable frequency range, up to 10 GHz, the antennae should be placed in the near field.

Not much literature exists regarding radar applications in near field and appropriate methods for the characterization of the antenna radiation pattern. The antenna radiation pattern is also subject to interferences caused by the body tissues under examination placed into the near vicinity of the antennae. The conventional approach of characterizing the antennae in a test range is not applicable, as the conditions in the test range are not matching the conditions of operation. Furthermore, the changes in propagation speed of the electromagnetic waves and incident reflections caused by the body tissue under examination requires an alternative in situ characterization method where the actual operating conditions are taken into account.

As the system is working in the near field, e.g. at frequencies whose wavelengths are in the same magnitude like the system's operating range, the information for the reconstruction of the image is mainly taken from the phase relationships between the incident wave transmitted by the antenna and the received signal reflected from the target. A SAR approach is used to increase the sensitivity by forming a large synthetic aperture by moving the antenna/antennae and collecting and processing the received data for multiple antenna locations. The antenna/antennae can move on an irregular path and the data acquisition can take place at non-uniform distances along that path. A complete reconstruction is possible as long as the path and the exact locations where the data acquisition took place are known.

For simplification the following description assumes a planar setup where one antenna is moved along a meander like path, illuminating a rectangular area on which the body tissue is placed. It is not important for the operation of the system that the antenna is moved along a planar surface, nor is the number of antennae limited to one, as long as the exact antenna positions in space are known.

A scan of the body part under examination is performed by moving the antenna along a meander like path. While the antenna is moving, electromagnetic waves are emitted into the body tissue at different frequencies, and the returned back scatter is recorded. As the beamwidth of the antenna is relatively large, all kinds of targets are illuminated and the corresponding backscatter recorded as long as the target lies within the beam of the antenna. By moving the antenna across the targets, the reflections caused by the cross section of individual targets are causing return signal which changes in a hyperbolic way as function of the lateral distance to the target. Several algorithms are available to reconstruct a 3d image from the information collected during the scan. One suitable reconstruction algorithm has been described in U.S. Pat. No. 6,061,589, Jack E. Bridges et al. Another reconstruction algorithm has been published in Lopez-Sanchez, J. M., Fortuny-Guasch, J., "3-D Radar Imaging using Range Migration Techniques," ISSN 0018-926X. These algorithms assume a well known uniform antenna radiation pattern, which can only be achieved in far field if the conventional approach for the antenna characterization is used.

If the system response can't be determined, a calibration procedure is used to calibrate the unknown system response to a known model. The calibration is performed by sequentially placing three calibration standards with different electromagnetic properties in front of the antenna setup, and measuring the radar cross section of each standard. If the antenna is physically moved to different locations during a scanning process, the measurements of the standards can be repeated for each antenna location to increase the accuracy of the calibration.

The data collected during the calibration measurements is used to calculate the error coefficients of the radar system, which are later used to remove the systematical errors of the system during operation. The calculation of the error terms basically determines the difference between the measured data of the calibration standards and the output of a mathematical model describing the behavior standards at different frequencies. Usually the calibration standards are chosen in a way to define three points of the Smith chart as the radar system can been seen as a one port measurement of the reflection coefficient.

Let assume that the standards used for the calibration are chosen as two reflection standards with total reflection and 180° phase offset ($\Gamma_{SO}=1$, $\Gamma_{SS}=-1$), defining the points 0 and ∞ of the Smith Chart—and a non reflecting standard matching the properties of the media the radar system is supposed to penetrate ($\Gamma_{SM}=0$).

The error terms used to describe the system response of the radar system can be calculated as follows:

$$E_s=[(\Gamma_{MS}*\Gamma_{SM}-\Gamma_{MM}*\Gamma_{SS})*(\Gamma_{SO}-\Gamma_{SS})-(\Gamma_{MS}*\Gamma_{SO}-\Gamma_{MO}*\Gamma_{SS})*(\Gamma_{SM}-\Gamma_{SS})]/[\Gamma_{MS}*\Gamma_{SS}*\Gamma_{SM}-\Gamma_{MM}*\Gamma_{SS}*\Gamma_{SM})*(\Gamma_{SO}-\Gamma_{SS})-(\Gamma_{MS}*\Gamma_{SS}*\Gamma_{SO}-\Gamma_{MO}*\Gamma_{SS}*\Gamma_{SO})*(\Gamma_{SM}-\Gamma_{SS})]$$

$$E_d=1/(\Gamma_{SM}-\Gamma_{SS})*(\Gamma_{MS}*\Gamma_{SM}-\Gamma_{MM}*\Gamma_{SS}-E_s*(\Gamma_{MS}*\Gamma_{SS}*\Gamma_{SM}-\Gamma_{MM}*\Gamma_{SS}*\Gamma_{SM}))$$

$$E_r=1/\Gamma_{SS}*(\Gamma_{MS}-E_d)*(1-E_s*\Gamma_{SS})$$

With
- $\Gamma_{SS}$: Complex value obtained from the model of reflecting standard S.
- $\Gamma_{SO}$: Complex value obtained from the model of reflecting standard O.
- $\Gamma_{SM}$: Complex value obtained from the model of non reflecting standard M.
- $\Gamma_{MS}$: Complex value obtained from the measurement of reflecting standard S.
- $\Gamma_{MO}$: Complex value obtained from the measurement of reflecting standard O.
- $\Gamma_{MM}$: Complex value obtained from the measurement of non reflecting standard M.
- $E_s$: Complex value for the uncorrected source match of the system.
- $E_d$: Complex value for the uncorrected directivity of the system.
- $E_r$: Complex value for the uncorrected tracking response of the system.

Knowing the values for $E_s$, $E_d$ and $E_r$ for each frequency emitted by the radar the system response can be equalized by applying the following formulas to each value of the received RCS data:

$$\Gamma=(\Gamma_r-E_d)/(E_r+(\Gamma_r-E_d)*E_s)$$

With
- $\Gamma_r$: Complex value for the uncorrected RCS received by the radar system.
- $\Gamma$: Complex value for the equalized RCS after error correction.

The error correction equalizes the system response needed for the matched filter to 1. The error correction is also removing the effects of multiple reflections caused by an encasement of the antenna as long as the calibration measurements include antenna and encasement. The error correction also removes the multiple reflections caused by a scan plate if the radar is used in an application where objects are scanned by moving the antenna along a predetermined path for imaging using a Synthetic Aperture Radar (SAR) algorithm.

In the latter case the calibration measurements can be taken in the same way at the same positions like the scanning of the objects is done, giving one set of error terms for each single antenna position. A further enhancement can be achieved by substituting the values obtained by the model of the non reflecting standard ΓMM with the averaged measurement data of several antenna locations around the antenna location to be error corrected, thus creating an adaptive error correction which automatically matches the electrical properties of the media the target is embedded in.

Therefore, the in situ antenna characterization presented herein may be implemented using a two-tiered approach. In a first step, several reflecting surfaces and at least one non-reflecting surface matching the surface of the antenna path at the skin interface of the body part under examination are scanned and the resulting data is stored. In a second step this error model is later used during an actual scan of the body part under examination to remove the systematic errors.

For example, the body part under examination itself is used as a non-reflecting surface, matching the system's performance exactly to the actual properties of the body tissue under examination.

FIG. 1 shows one form of the system 10. The system 10 includes an antenna 12, an air gap 14 between the antenna 12 and a non conducting plate 16 which has a bottom surface 18 and top surface 20. The top surface 20 forms the surface at which the calibration measurements are performed and which is also the surface on which the breast tissue is placed to perform the scan. One of the measurements may be made with the top surface 20 left completely open to form an RF reflective surface at the top surface 20 of the plate 16 as the electromagnetic waves are travelling from an area of higher dielectric properties (scan plate) into an area with lower dielectric properties (air), the phase of the reflected signal shifts by a well-defined amount. This measurement is made to form a reference to remove systems errors due to reflections at the surface. The system also includes a calibrator 21.

Figure 2:
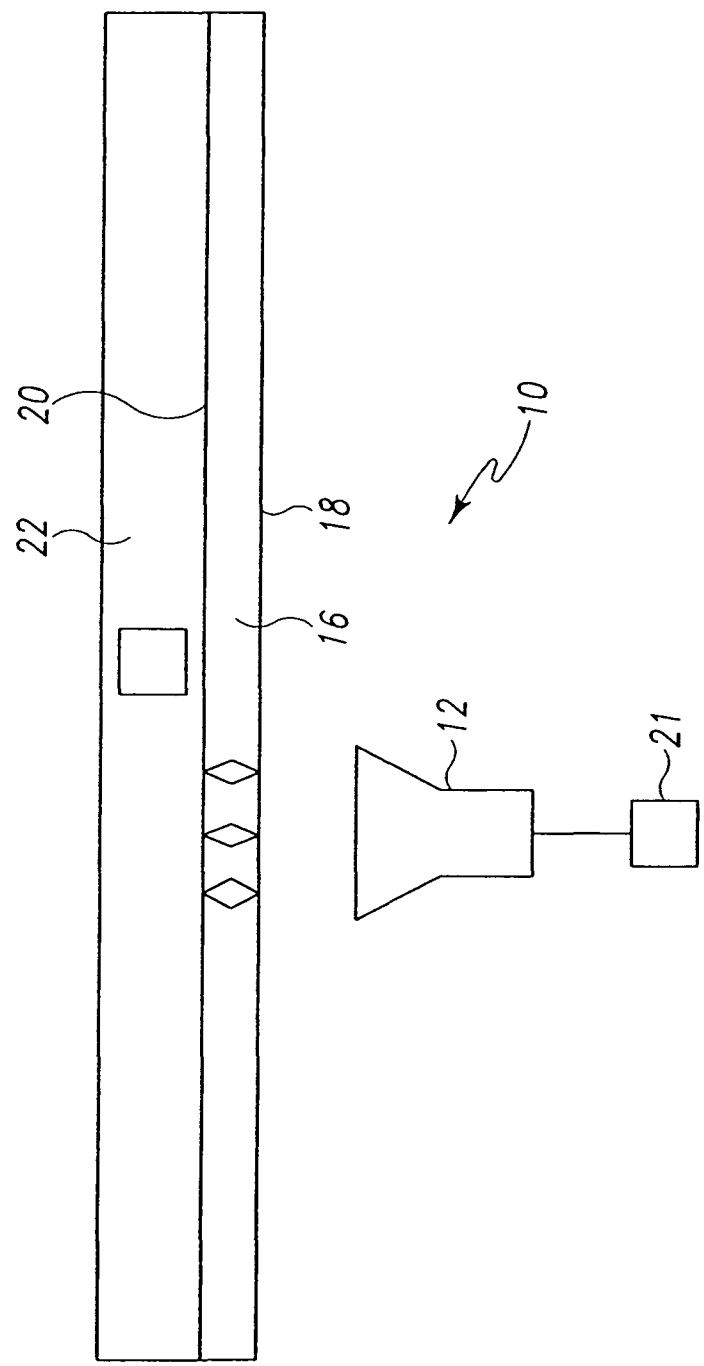
FIG. 2 is a somewhat schematic representation showing a radar system with an RF non-reflecting material.

FIG. 2 shows the placement of an RF non-reflecting material 22 placed on the top surface 20 of the plate 16. This is another form in which a measurement is made to calibrate or measure the system response at the surface with a material that is not reflective.

Figure 3:
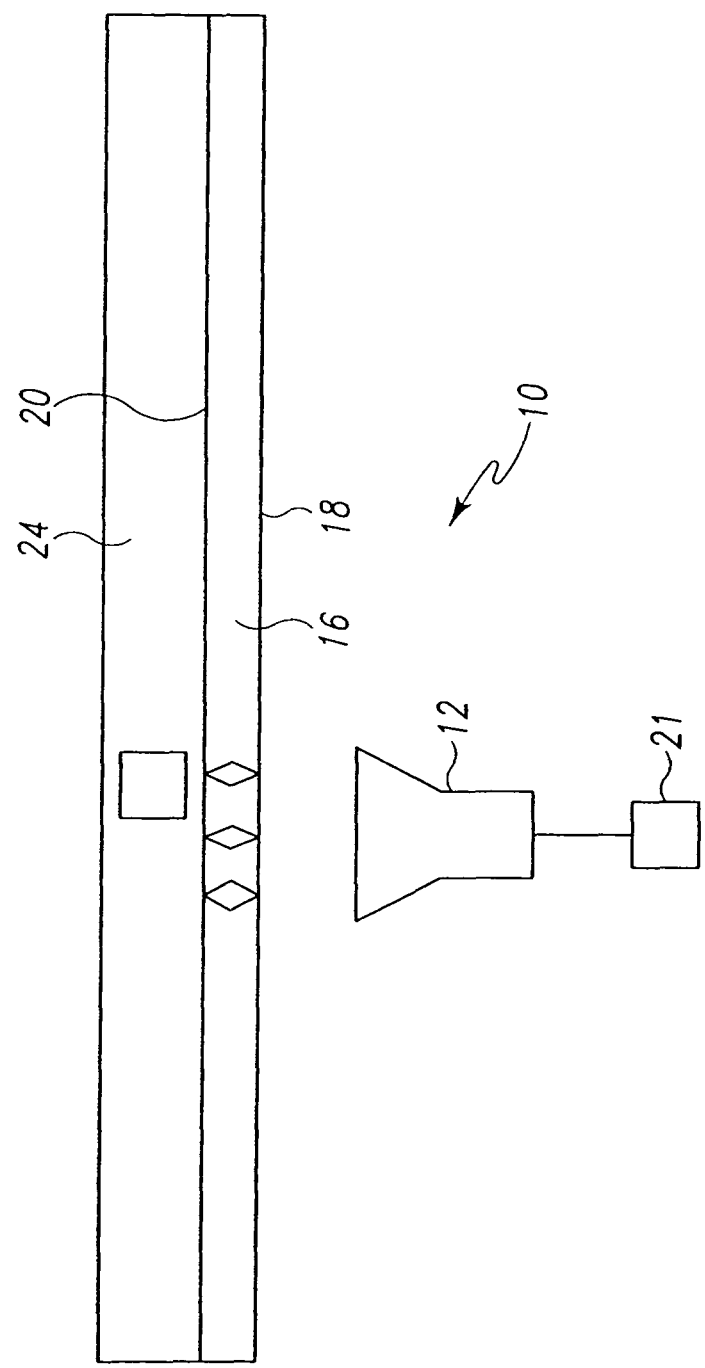
FIG. 3 is a somewhat schematic representation showing a radar system with a conducting reflective material.

FIG. 3 shows a conducting reflective material 24 placed on the top surface 20 of the plate 16. In this case the reflection takes place again at the boundary between two materials with different dielectric properties, but this time the phase is shifted by another well-defined amount specified by the dielectric properties of the reflective surface. If the same reflective surface is placed on the surface with an air gap 26 between the conducting reflective material 24 and the top surface 20 of the plate 16, the phase shift changes by a fixed amount which is defined by the width of the air gap.

From the different phase/magnitude values taken for a specific frequency when the different known surfaces are used or the surfaces are applied with different known air gaps, the absolute phase and magnitude of the radar system's transfer function can be calculated for that specific frequency. In repeating the calibration steps for all frequencies used by the radar system, the wideband transfer function of the radar system including the antenna and object brought statically into the beam of the antenna (like the scan plate) can be calculated and an error model is derived from that transfer function for later error correction of the measurements of the body tissues.

Figure 4:
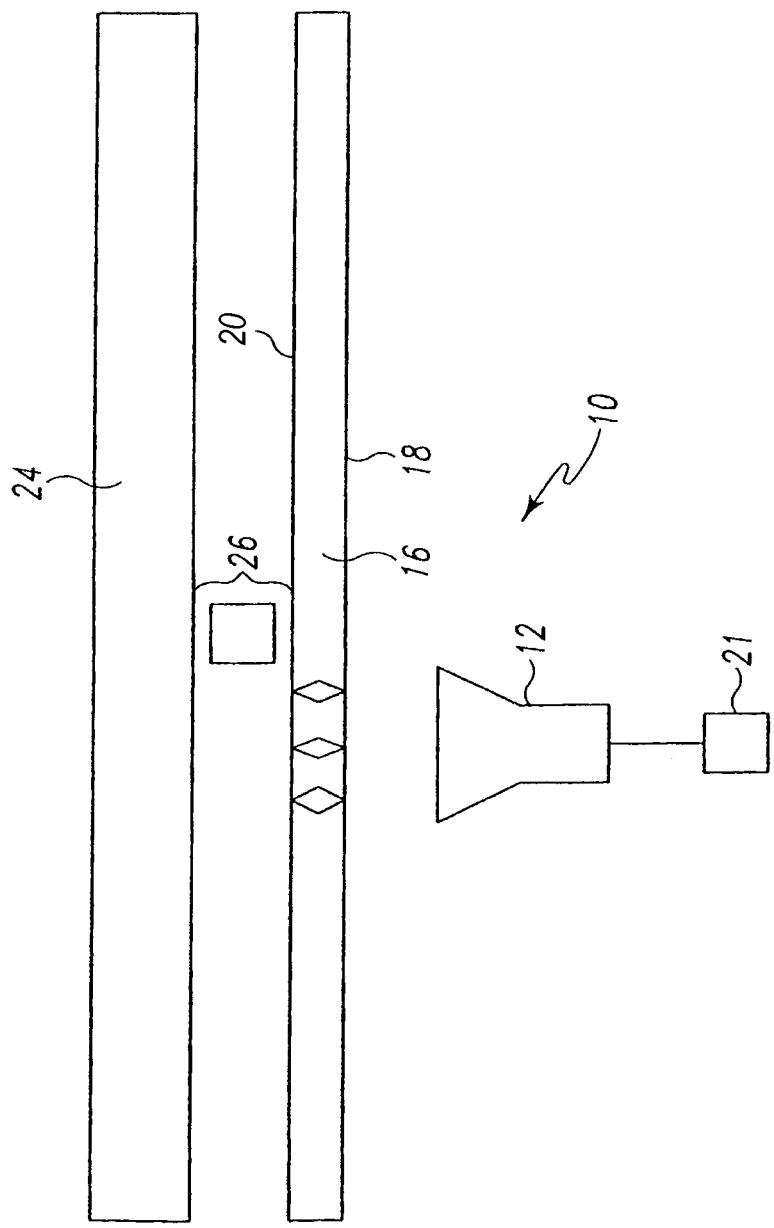
FIG. 4 is a somewhat schematic representation showing a radar system with an air gap between the conducting reflective material and the scan plate.

FIG. 4 shows the conducting reflective material 24 placed on surface with an air gap 26 between the conducting reflective material 24 and the top surface 20 of the plate 16. A measurement to remove systems errors may also be done using conductive reflecting surfaces at more than one distance from the top surface of the plate 16, thereby varying the air gap 26. While the distance of the air gap 26 is not critical, it should be a significant portion of a wavelength of the highest frequency used to make measurements so that the significant difference in the phase angle of the returned signal relative to measurement taken when the air gap is set to zero as in FIG. 3.

Figure 5:
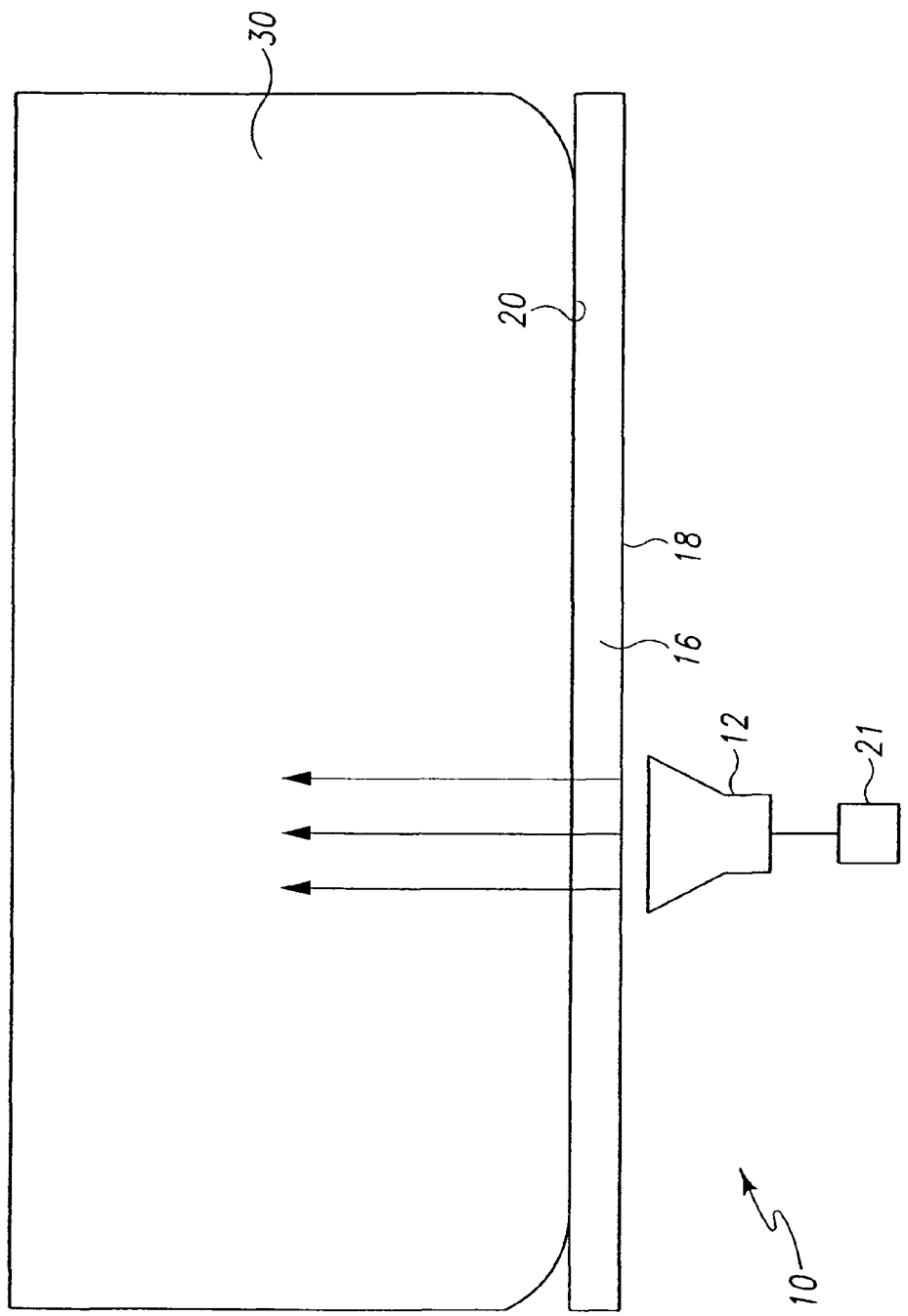
FIG. 5 is a somewhat schematic representation showing a radar system with human tissue.
Figure 6:
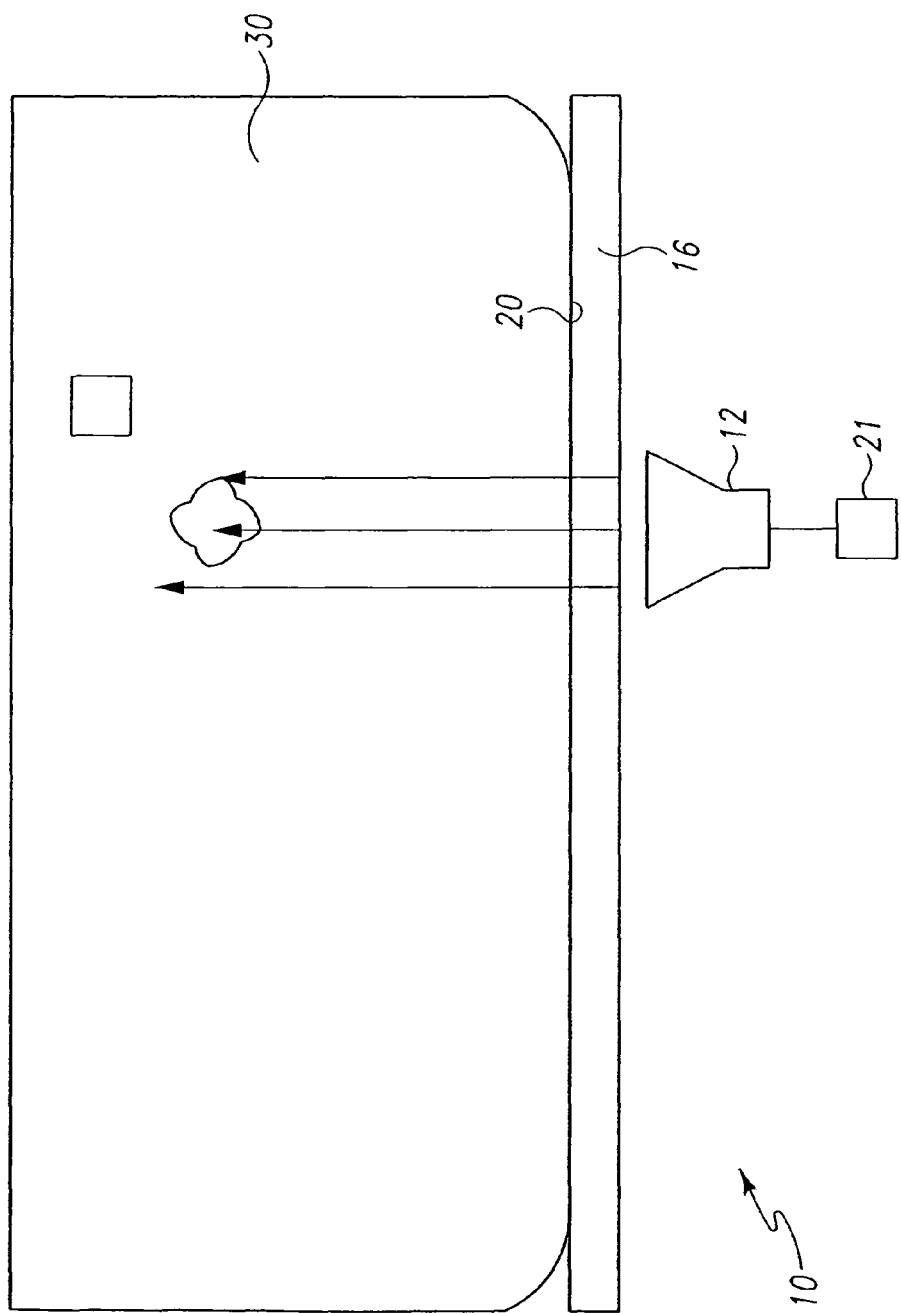
FIG. 6 is a somewhat schematic representation showing a radar system with human tissue having cancerous tissue.

FIG. 5 shows body tissue 30 used as a reference to remove system errors. This may be used in place of the RF non-reflecting material 24 as shown in FIGS. 3 and 4. FIG. 6 shows a cancerous tissue 32 imbedded in the body tissue 30 and having different reflection properties being detected by the system 10.

In using the body tissue as a reflecting surface the scan plate/skin boundary for that individual sample under test can be included into the error model. As the dielectric properties of human tissues are different from individual to individual, even when sampling the same body parts, an inclusion of the true dielectric properties into the error model is preferable.

After all surfaces have been processed, the collected data is used to calculate an error model of the radar system including the antenna describing the effects caused by the distortion of the antenna radiation pattern, by unwanted reflections inside the antenna and from the system itself over frequency and antenna location. These errors are called the systematic errors as they are caused by the properties and components of the system itself, like the frequency response of transmitter, receiver, or the frequency response and radiation pattern of the antenna, or the thickness and material of the scan plate 16, or the air gap between the antenna and the scan plate 16.

In the second step the error model is used during an actual scan of the body part under examination to remove the systematic errors. In this way the sensitivity of the system is greatly enhanced as the effects of the distortion of the antenna pattern and unwanted reflections is not masking the weak returns from the actual target anymore. Furthermore, the improved uniformity of the antenna's phase relationship after error correction improves the quality of the reconstruction algorithm. The reconstruction algorithm is used to form a 3D picture from the error corrected measurement data after the error correction has been already been performed.

The calibration procedure when a planar surface is used as the tissue interface is straight forward. A conducting metal surface is placed on the surface and the system is told to take the measurement. An RF absorbing material can also be placed on the surface and used as another reference. A third reference can be obtained by placing nothing on the surface and detecting just the background reflections. When calibrating using a non-coplanar interface, such as shape formed around the tissue, the tissue to be examined can be wrapped in a metalized mylar film to form one of the reflection standards. An absence of the tissue can be utilized as the second reflective calibration standard and lastly the tissue itself can be used as the absorption standard. If the tissue can be easily shaped to fit a form, the same calibration techniques can be used as used for the co-planer interface with the reflecting and absorbing materials made to fit the form to make the calibration measurements. A form made in the shape of a bra to fit the human breast may be used instead of a flat plate. There may be a number of different size forms pre-made to fit most patients. A conducting reflecting insert and an absorbing insert made to fit directly against the form where the breast tissue will make contact will be used in the calibration procedure in lieu of the flat ones used when calibrating the system when a flat coplanar plate is used.

One aspect of this concept is the use and calibration of a SAR system used in the near field to develop a three dimensional image of tissue, as opposed to the current systems which only can operate when used in the far field. The near field SAR system when properly calibrated can provide the same images as obtained by far field SAR systems. The use of a calibration technique that is calibrated at the point of contact with the tissue provides the best system for removing errors from unwanted reflections, antenna patterns and all other issues with related to measurements of RF and microwave reflections from objects. Because this equipment can operate effectively in the near field, the microwave frequencies can be much lower than other equipment that must operate in the far field to be effective. The frequencies utilized in the preferred embodiment are discrete stepped frequencies between 1.2 GHZ and 8 GHZ but are not limited to this band.

This technique allows for a simpler system that does not require a means to determine where the tissue surface is located as the system can be calibrated at the tissue surface with ease. In the case of a far field measurement, determining the surface of the tissue is essential to forming a three dimensional image of the tissue and eliminating the reflections from the air-breast surface interface or if a liquid or get dielectric is utilized, the interface between it and the breast. Near field measurements are made feasible by placing the tissue at a known location at which system errors have been removed through calibration. This technique allows for and is not adversely affected by an air gap between the antenna and a plate if used to form the surface on which the breast is placed. The air gap need not be uniform and distance from the antenna to the surface of the breast is not critical. While not allowing for relatively free form positioning of the patient as in far field SAR systems, the near field SAR is particularly suited to producing an image of the human breast wherein the breast tissue can be placed in contact with the surface at which the calibration was performed. It does not require the breast to be flattened or squeezed as in X-ray mammograms but allows patient to just lie face down so that the breasts are in a known position. In one embodiment of this invention the tissue surface may be made to conform to a flat surface in which tissue such a breast tissue is brought into contact with the surface at which calibration was performed. In another embodiment, the surface at which calibration is performed has been formed to match the shape of the tissue. This imaging system has been shown to detect cancerous tissue where X-ray technology was unable to do so. It also is capable of discerning between calcium deposits and other abnormalities normally associated with cancer.

The system and method does not preclude the use of any particular SAR antenna system and does not in particular require antenna characterization as required for far field SAR systems. The various embodiments include a single movable antenna, separate transmit and receive antennae, an array of transmitting and or receiving antennae in which signals are steered to create the synthetic aperture.

This system and method may eliminate the necessity to maintain a focal ratio of unity to determine the distance from the antenna/antennae to the tissue as is necessary to minimize the degrading of the size of the synthetic focal spot. This system and method may also eliminate the requirement to keep the antenna system at approximately the same distance from the breast surface throughout the process in order to maintain a system calibration required for accurate measurements and display of image. Thus the antenna system may operate in a planar manner and yet produce detailed 3 dimensional images.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicants' contribution. The actual scope of the protection sought is intended to be defined in the following claims when viewed in their proper perspective based on the prior art.

What is claimed is:

1. A method for calibrating a near field synthetic aperture radar system, the method comprising the steps of:
   positioning at least one antenna adjacent an object to be scanned in a near field relationship;
   scanning a reflecting material using the at least one antenna at a plurality of antenna locations to create a scanning profile, the scanning profile being created from a reflected wave having a local non-planar wave front when received at the at least one antenna;
   scanning an absorbing material using the at least one antenna at a plurality of antenna locations to create an absorbing profile, the absorbing profile being created from a reflected wave having a generally local non-planar wave front when received at the at least one antenna; and
   creating a calibrated profile using the scanning profile and the absorbing profile, the calibrated profile including an error model that describes at least the effects caused by distortion of a radiation pattern of the at least one antenna for the plurality of antenna locations in a near field relationship with an object to be scanned, the error model being based on the scanning profile and the absorbing profile.

2. The method of claim 1 wherein the at least one antenna is positioned a distance from the object to be scanned, the distance defining an air gap.

3. The method of claim 1 further comprising the steps of scanning human tissue to create an uncalibrated profile and creating a corrected profile using the calibrated profile and uncalibrated profile.

4. The method of claim 3 wherein the corrected profile is a three-dimensional profile.

5. The method of claim 1 wherein multiple antennae are positioned.

6. The method of claim 1 wherein the step of creating the calibrated profile includes a single port calibration method.

7. The method of claim 1 wherein the step of creating the calibrated profile includes a multiple port calibration method.

8. The method of claim 1 wherein the at least one antenna is movable for scanning at multiple positions.

9. The method of claim 1 wherein the positions of a single antenna or multiple antennae define a geometric plane at points where measurements are made.

10. The method of claim 1 wherein the positions of the antenna or antennae define a three dimensional object that is not a geometric plane at the points at which measurements are made.

11. The method of claim 1 wherein the absorbing material is human tissue.

12. A system for determining localized differences in human tissue comprising:
    at least one antenna for transmitting and receiving a signal in near field uses;
    a reflecting material positioned adjacent the at least one antenna in a first calibration configuration and in a near field relationship;
    an absorbing material positioned adjacent the at least one antenna in a second calibration configuration and in a near field relationship; and
    a calibrator, wherein in the first calibration configuration, the calibrator is configured to create a scanning calibration profile from a reflected wave having a local non-planar wave front when received at the at least one antenna at a plurality of antenna locations, when in the second calibration configuration, the calibrator is configured to create an absorbing calibration profile from a reflected wave having a local non-planar wave front when received at the at least one antenna at a plurality of antenna locations and the calibrator is configured to determine an error model that describes at least the effects caused by distortion of a radiation pattern of the at least one antenna for the plurality of antenna locations in a near field relationship with an object to be scanned, the error profile being based on the scanning profile and the absorbing profile.

13. The system of claim 12 wherein the at least one antenna is positioned a distance from the object to be scanned, the distance defining an air gap.

14. The system of claim 12 wherein human tissue is scanned to create an uncalibrated profile and the calibrator creates a corrected profile using the uncalibrated profile and the error profile.

15. The system of claim 14 wherein the corrected profile is a three-dimensional profile.

16. The system of claim 12 wherein the calibrator uses a single port calibration method.

17. The system of claim 12 wherein the calibrator uses a multiple port calibration method.

18. The system of claim 12 wherein the at least one antenna is movable for scanning at multiple positions.

19. The system of claim 12 wherein the at least one antenna is coplanar.

20. The system of claim 12 wherein the at least one antenna is non-coplanar.

21. The system of claim 12 wherein the absorbing material is human tissue.

22. The system of claim 12 wherein the antenna is printed on a flexible material.

* * * * *